United States Patent [19]

Ball et al.

[11] 4,059,009
[45] Nov. 22, 1977

[54] LIQUID CHROMATOGRAPHY SYSTEM

[75] Inventors: Dean M. Ball, Norcross; Warren P. Hendrix, Lawrenceville, both of Ga.

[73] Assignee: Micromeritics Instrument Corporation, Norcross, Ga.

[21] Appl. No.: 722,163

[22] Filed: Sept. 10, 1976

[51] Int. Cl.² ........................................... G01N 31/08
[52] U.S. Cl. ............................ 73/61.1 C; 73/422 GC
[58] Field of Search ...................... 73/61.1 C, 422 GC

[56] References Cited

U.S. PATENT DOCUMENTS

| | | | |
|---|---|---|---|
| 3,411,525 | 11/1968 | Auger | 73/422 GC |
| 3,864,978 | 2/1975 | Stephens | 73/422 GC |
| 3,916,692 | 11/1975 | Abrahams et al. | 73/422 GC |
| 3,961,534 | 6/1976 | Gundelfinger | 73/422 GC |

Primary Examiner—Charles A. Ruehl
Attorney, Agent, or Firm—Jones, Thomas & Askew

[57] ABSTRACT

Improved method and apparatus for injecting a predetermined amount of a sample liquid into a high pressure stream of carrier liquid for introduction into a liquid chromatography column, wherein the flow of high pressure carrier liquid in the column is maintained at a substantially constant pressure and rate of flow, including periodically accumulating a precise amount of sample liquid in a primary flow path of carrier liquid to the column while automatically diverting all of the carrier liquid into a secondary flow path to the column in response to a small increase in carrier liquid pressure upstream of the sample accumulation point. Also disclosed is a three position, rotary sample injection valve having improved sealing means for introducing a sample liquid into a high pressure carrier liquid.

9 Claims, 8 Drawing Figures

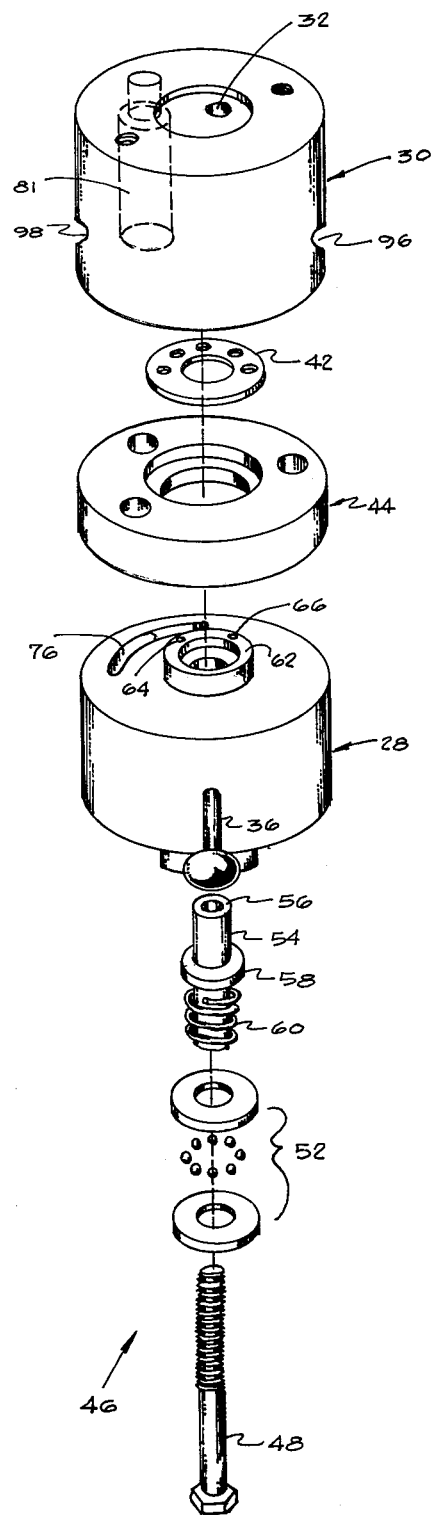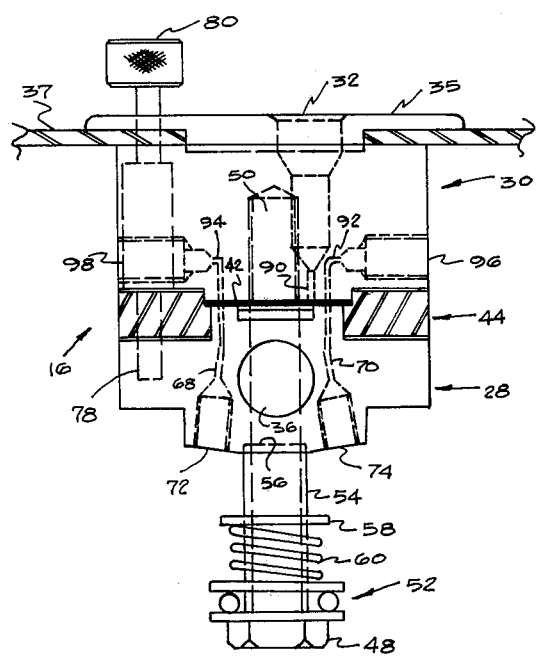
FIG. 2
FIG. 3

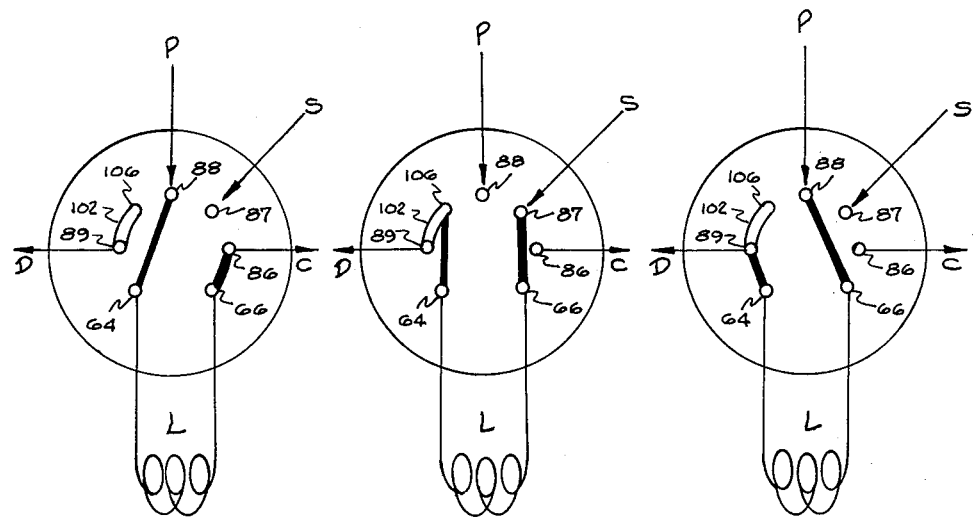

LIQUID CHROMATOGRAPHY SYSTEM

BACKGROUND OF THE INVENTION

This invention relates in general to the field of chromatography and in particular to an improved method and apparatus for use in the field of liquid chromatography.

Chromatography is recognized by those skilled in the art as a procedure for analyzing a sample through the steps of passing the sample through a body of material and detecting the relative separations of various sample substances which occur during such passage. In the specific field of liquid chromatography, the sample undergoing analysis may typically be introduced into a carrier liquid which is passed through a chromatography column containing material which adsorbs components of the liquid being analyzed. The extent to which these different components are adsorbed in the column is determined by a suitable detector connected to analyze the liquid effluent from the column.

Those familiar with the art of liquid chromatography are aware that it is highly desirable to provide a flow of carrier liquid which is delivered to the chromatograph column at a constant rate of flow and which is free of any appreciable pressure pulsations. The presence of pressure pulsations in the carrier liquid supplied to the chromatograph column can vary the rates of adsorption occurring within the column, and thus can provide a false indication of the adsorption of constituents in the sample being analyzed. These false indications amount to "noise" in the detector output, and this noise masks or otherwise obscures bona fide signals whose amplitude is not significantly greater than that of the pulsation-induced noise. The effective sensitivity of a liquid chromatograph can be increased, accordingly, by reducing the pressure pulsations in the carrier liquid. Various pumping means may be employed to deliver high pressure carrier liquid at constant flow rates with minimum pressure pulsations, and one such liquid chromatography system employing substantially constant flow and pressure pumping means is disclosed in U.S. Pat. No. 3,932,067, issued Jan. 13, 1976.

In liquid chromatographic analysis, it is a practice to first establish a flow of high pressure carrier liquid through the chromatography column and then to introduce a precisely measured volume of sample liquid into the flow stream so that it is carried to the column for separation and subsequent analysis. One approach to sample introduction involves the use of a syringe injection method wherein a syringe containing a precise amount of sample liquid is injected through an elastomeric septum directly into the carrier flow path. However, direct sampling injection has a disadvantage, in that, the elastomeric septum is often incompatible with many carrier liquids. Also, because of the high operating pressures of the carrier liquid, e.g., pressures as much as 1,000 psi, special syringes with high pressure capabilities must be employed.

Another approach to sample introduction involves the use of sample injection valve having a liquid-holding sample loop, or conduit, of fixed volumetric capacity, which is normally external of the carrier liquid conduit and which may be charged with a desired predetermined volume of sample fluid. The valve is then actuated to connect the external sample loop into the carrier liquid circuit and the sample previously disposed in the loop is carried to the separation column. One such sample injection valve mechanism utilizing an external sample loop to introduce a predetermined measured amount of sample liquid into a diverted portion of a pressurized carrier liquid stream is disclosed in U.S. Pat. No. 3,916,692.

Since it is necessary for accurate sample analysis that the high pressure liquid through the column be free of any appreciable flow and pressure variations, it is highly desirable that the liquid sample be introduced into the carrier liquid without creating any pressure or flow variations which would disrupt the analysis of the sample. It can be understood that when a small sample of specimen of liquid is momentarily introduced from an external storage source by valving means into the high pressure carrier liquid, a large pressure variation can occur in the liquid stream as a result of the valve-switching operation with detrimental effects to the analysis obtained by the apparatus. This is particularly true when the storage source is filled and maintained at substantially atmospheric pressure before its introduction into the high pressure carrier flow stream.

Due to the high pressures employed in the carrier system, it is also desirable to insure that the sample injection valve mechanism for introducing the sample liquid is maintained free from leakage both during the accumulation of a precise amount of the sample, as well as during introduction of the sample into the carrier liquid stream. Furthermore, to insure that precise amounts of liquid sample are delivered to the chromatography column, it is essential that the sample injection valve mechanism be such as to minimize the dead space in which liquid sample is retained upon injection of the liquid sample into the carrier liquid stream.

SUMMARY OF THE INVENTION

It is therefore an object of the present invention to provide an improved apparatus for use in liquid chromatography which eliminates any appreciable pressure variations in the system during sample introduction.

It is another object of the present invention to provide improved injection means for introducing sample liquid into a liquid chromatography system wherein the sample may be readily accumulated in a precise volume at substantially atmospheric pressure, and can thereafter be introduced by valve means into the high pressure carrier liquid stream without pressure variation, without significant loss of sample in the valve means, and in a high speed, leak-free, reliable manner.

It is a further object of the present invention to provide an improved method of introducing precisely measured amounts of sample liquid into a chromatography column for separation and analysis.

The above we well as other objects of the present invention are accomplished by the provision of a liquid chromatography system including a source of pressurized carrier liquid, conduit means for supplying the carrier liquid to a chromatography column, a rotary switching valve positioned in said conduit means for selectively introducing a liquid specimen sample into the pressurized carrier liquid and having substantially no dead space in which sample is retained, and a pressure-actuated valve in said conduit means for providing carrier liquid to the chromatography column with substantially constant flow and pressure of the carrier liquid to the column at all times during collection and introduction of the sample into the carrier stream.

The sample injection valve of the present invention comprises a three position, rotary switching valve having two ports in the rotor communicating by passageways with opposite ends of a sample storage loop, and having four ports in the stator for communicating opposite ends of the sample loop, respectively, with (1) a sample insertion inlet and an "overflow", or discharge, line to waste wherein the sample loop may be filled with a precise amount of sample liquid, (2) a pressurized source of carrier liquid and the chromatography column wherein the accumulated sample liquid is introduced into the system, and (3) the pressurized source of carrier liquid and the overflow line wherein the sample loop is cleaned with carrier liquid prior to accumulation of a new sample liquid. The invention also provides a pressure-actuated valve located in a secondary carrier flow conduit of the chromatography system which is in parallel with the sample injection valve to automatically direct the entire flow of carrier liquid to the chromatography column in response to a very small pressure rise in the upstream carrier liquid when the injection valve is switched into a sample load position, and to automatically close the secondary conduit in response to a very small pressure drop in the upstream carrier liquid to redirect all of the carrier liquid through the injection valve when the valve is switched into a sample inject position.

BRIEF DESCRIPTION OF THE DRAWINGS

The above as well as other objects of the invention will become more apparent, and the invention will be better understood from the following detailed description of a preferred embodiment of the invention, when taken in conjunction with the accompanying drawings in which like parts are designated by the same numeral in each figure, and in which:

FIG. 2 is an exploded, perspective view of the sample injection valve of the present invention;

FIG. 3 is a front elevational view of the assembled valve of FIG. 2, with a portion of the valve shown in section and certain of the interior liquid flow passages of the valve shown by invisible lines;

FIGS. 6, 7 and 8 are schematic diagrams illustrating the flow paths of the liquid through the injection valve when the valve is positioned in a sample inject position, a sample load position, and a sample loop clean position, respectively.

DESCRIPTION OF THE PREFERRED EMBODIMENT

Figure 1:
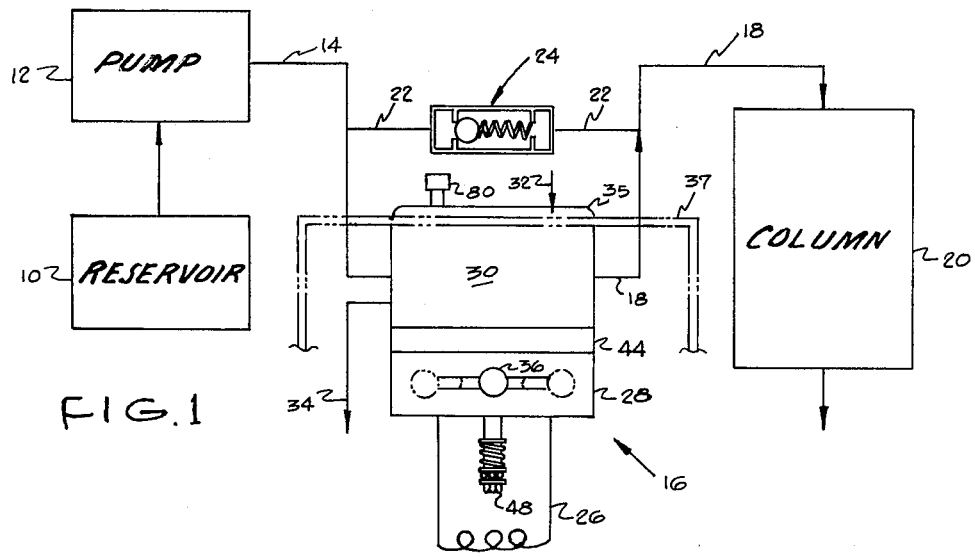
FIG. 1 is a block flow diagram of a liquid chromatography system according to the preferred embodiment of the invention, and showing the liquid flow path between the various components of the system.

Referring more specifically to the drawings, FIG. 1 is a schematic block diagram of the component parts of the chromatography system of the present invention. As illustrated thereby, a carrier liquid is delivered at a predetermined high pressure from a reservoir 10 by suitable pumping means 12 through a primary flow conduit 14 which communicates with an inlet of a sample injection valve 16. The valve 16, in turn, communicates by way of an outlet and primary flow conduit 18 with a chromatography column 20. Connected between the primary conduits 14 and 18 is a secondary conduit 22 in which is located a pressure-actuated valve 24. The secondary conduit 22 and pressure-actuated valve 24 are thus positioned in parallel arrangement with the injection valve 16 to deliver all carrier liquid flow from pumping means 12 directly to the chromatography column during certain periods of operation of the sample injection valve 16, as will be explained. A sample liquid storage loop, or conduit, 26 is connected to the rotor section 28 of injection valve 16, and the stator section 30 is provided with an inlet 32 for introducing a liquid sample into the sample loop carried by the rotor section, and an outlet connected to an overflow, or discharge, to waste conduit 34. The rotor 28 is also provided with a handle 36 to permit manual positioning of the valve between three positions—(1) a loop cleaning position wherein the handle is located as shown by the right-hand phantom line handle position in FIG. 1, (2) a sample load position, as shown by the center, solid line handle position of FIG. 1, and (3) a sample injection position, as shown by the left-hand, phantom line handle position of FIG. 1. The flow paths of the liquid through the injection valve in each of its three valve positions will be fully explained as the description proceeds. The stator section 30 of the injection valve 16 is provided with an upper circular cap member 35 (FIGS. 1 and 3), and the cap and main body of the stator section are supportably attached by suitable means, such as screws (not shown), to a support plate 37 (shown in phantom lines in FIG. 1 and in section in FIG. 3).

FIG. 2 is an exploded, front perspective view of the sample injection valve 16 showing, in vertically spaced relation, the stator section 30, an annular valve-sealing gasket 42, a gasket locking ring 44, the rotor section 28, and fastening means, generally indicated as 46, which maintain the stator and rotor sections in operative, rotatable engagement. Fastening means 46 comprises a threaded bolt 48 which extends through a respective central openings in the rotor, locking ring, and the gasket, and is threadably received into an internally threaded central opening 50 (FIG. 3) of stator section 30. The threaded bolt 48 carries a ball-bearing ring 52 and a sleeve element 54, the upper surface 56 of which abuts the lower surface of the rotor section 28 (FIG. 3). The sleeve element is provided with a peripheral flange 58 and a compression spring 60 is positioned between the flange and bearing to exert a biasing force against the rotor section to maintain it in engagement with the stator section during positional rotation of the valve.

The gasket locking ring 44 is secured to the stator section by suitable means such as fastening screws (not shown) to retain the sealing gasket 42 in engagement with the lower valve face of the stator. The rotor and stator sections of the valve may be formed of suitable material, such a stainless steel or the like, which is of sufficient strength to withstand the operating pressures and handle the various liquids employed in the chromatography system.

Figure 5:
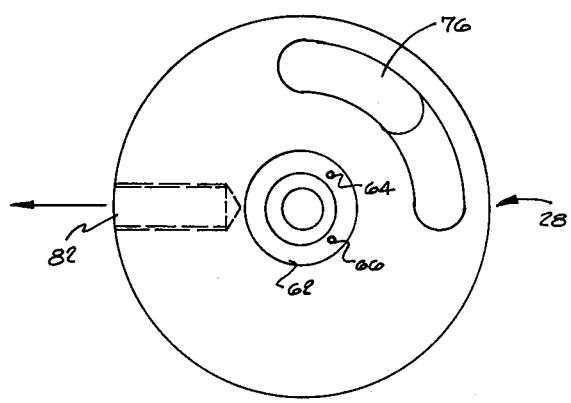
FIG. 5 is a top plan view of the top face of the rotor section of the injection valve as seen in FIGS. 2 and 3, with interior portions thereof shown by invisible lines, the front of the valve being indicated by an arrow.

As best seen in FIGS. 2, 3 and 5, the upper face of the rotor 28 is provided with a raised flat, annular surface 62 (FIG. 2) containing two ports, 64, 66 which are positioned at 90° from each other about annular surface 62 and communicate by passageways 68, 70 (FIG. 3) extending through the rotor section with respective openings 72, 74 in the lower face of the rotor. Openings 72, 74 receive opposite ends of the sample loop conduit 26.

As shown in FIGS. 2 and 5, the upper face of the rotor section is also provided with an arcuate stepped slot, or groove, 76 which extends about the face throughout a 90° arc and receives the lower end 78 of a locking pin 80 which is carried by and extends through a vertical passageway 81 in the stator section and gasket locking ring 44. The locking pin is vertically movable in the stator section and is biased in a downward direction, to retain the lower end 78 of the locking pin in the rotor groove 76, by suitable spring means (not shown) positioned inside the stator. The purpose of the locking pin is to facilitate the positive positioning of the rotor section of the injection valve in each of its three positions of operation, as will be explained. As also seen in FIGS. 3 and 5, the operating handle 36 for rotating the valve is threadedly secured in an internally threaded opening 82, in the side of the rotor.

Figure 4:
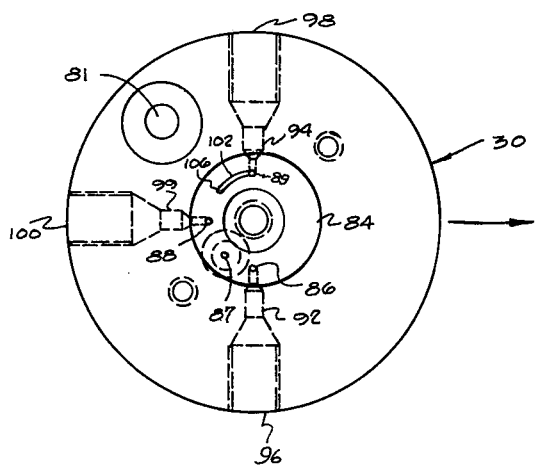
FIG. 4 is a bottom plan view of the bottom face of the stator section of the injection valve as seen in FIGS. 2 and 3, with the interior liquid flow passages thereof shown by invisible lines, the front of the valve being indicated by an arrow.

As seen in FIGS. 3 and 4, the bottom face of the stator section is provided with a centrally located annular flat surface 84 (FIG. 4) which overlies the annular flat surface 62 of the rotor in mating relation thereto (FIG. 3). Surface 84 is provided with four ports, 86–89, which are arcuately spaced about the surface from each other. Port 87 communicates by a vertical passageway 90 (FIG. 3) with sample inlet opening 32 in the upper surface of the stator to permit introduction of an amount of sample liquid specimen into the sample loop 26 of the rotor section. Ports 86 and 89, which are positioned 180° apart on the annular surface 84, communicate by way of respective passageways 92 and 94 which extend from the ports upwardly (FIG. 3) and then outwardly (FIG. 4) to respective openings 96, 98 in the opposite sides of the stator section. Opening 96 communicates by way of conduit 18 with the chromatography column 20, and opening 98 communicates with the overflow of waste conduit 34. Port 88, positioned 90° from each of the ports 86, 89 communicates by way of a passageway 99 extending upwardly and then outwardly to a side opening 100 of the stator section. Opening 100, in turn, communicates by conduit 14 to receive pressurized carrier liquid from pumping means 12 (FIG. 1). Each of the inlets and outlets of the injection valve are so constructed as to receive and retain the various conduits of the chromatography system by conventional fastening means or connecting means located on the ends of the conduits. The sample storage loop conduit is of fixed predetermined volume.

As seen in FIG. 4, the flat surface 84 of the stator section is also provided with an arcuate groove 102 which communicates with and extends for a 45° arcuate distance about the annular surface from port 89. The groove 102 serves as a liquid passageway to communicate the overflow discharge conduit 34 with an end of the sample loop 26 when the rotor of the valve is placed in the sample load position, as will be explained.

Positioned between the mating annular surfaces 84 and 62 of the stator and rotor is the annular gasket 42 which is held in engagement with the stator surface 84 by the annular clamping ring 44. The gasket is provided with five holes therethrough which, when the gasket is positioned on the stator surface 84, are located in respective alignment with the four ports of the stator surface and the end 106 of the arcuate groove 102 therein. The holes provide communication between the rotor and stator ports when they are selectively aligned in one of the three positions of the valve, and the gasket serves to prevent the escape of liquid from all of the ports of the stator and rotor sections when they are not in selective alignment. The gasket 42 comprises a plastic material such as graphite-impregnated Teflon or the like which is impervious to carrier liquids typically used in liquid chromatography and has sufficient rigidity to maintain its shape under the pressure of the flow of carrier liquid through the valve 16.

To insure that the holes of the gasket are always maintained in proper alignment with the corresponding ports of the stator, the stator surface is left in an unpolished state having a relatively high coefficient of friction. Correspondingly, to insure free movement between the lower surface of the gasket and the rotor surface 62, the rotor surface 62 is provided with a highly polished surface having a relatively low coefficient of friction. Thus, the gasket can be positively retained in its proper position on the surface of the stator, while the rotor is free to move with respect thereto.

The liquid flow paths through the injector valve in each of its three positions of operation will be best explained by reference to the flow path diagrams illustrated in FIGS. 6–8. Each of the FIGS. 6–8 show diagramatically, in circularly positioned arrangement, the stator ports 86–89 and rotor ports 64, 66 of the injection valve 16. It is to be understood that the stator ports 86–89 communicate by their respective passageways in the stator section with the pump inlet conduit 14, the sample inlet 32, the column outlet conduit 18 and the discharge to waste conduit 34 in the manner previously described, while the rotor ports 64 and 66 communicate by their respective passageways in the rotor section with the sample loop conduit 26 in the manner also previously described. For convenience of explanation, these various passageways and conduits have not been shown in detail in the diagrams of FIGS. 6–8, but their presence is represented by the arrow lines P, S, D, C and L connected with the respective ports illustrated. The alignment of the various ports in each of the three valve positions are indicated by solid block lines connecting the ports in the respective figures.

FIG. 7 illustrates the liquid flow path through the injection valve when the valve is in "sample load" position with rotor handle 36 located in the center position shown in FIG. 1. In this position, rotor port 64 is aligned with the end 106 of the liquid flow groove 102 in the stator and rotor port 66 is aligned with stator port 87. In this position of the valve, an amount of liquid sample to be analyzed is introduced through the sample inlet S to completely fill the sample loop L with excess sample liquid overflowing to waste D by way of groove 102 and port 89 in the stator section of the valve. Since the sample loop L is of a selected, predetermined volume, a precise amount of liquid sample is collected in the sample loop for introduction into the chromatography column. The sample liquid may be introduced into the sample inlet by suitable means, such as a syringe, while the sample loop is under substantially atmospheric pressure.

FIG. 6 illustrates the liquid flow path through the injection valve when the valve is in "sample inject" position with rotor handle 36 located in the left-hand position, as shown in phantom lines, in FIG. 1. In this position, rotor port 64 is aligned with stator portion 88 and rotor port 66 is aligned with stator port 86. In this position of the valve, high pressure carrier liquid is delivered from the pumping means P through the sample loop L and to the column C. The sample liquid stored in the sample loop L is thus transported into the column by the carrier liquid for separation and analysis.

As can be seen, when the injection valve is in the "sample load" position (FIG. 7), no high pressure carrier liquid passes through the injection valve, but all such carrier liquid is directed by way of auxiliary conduit 22 and pressure-actuated valve 24 directly to the column 20 (FIG. 1). The pressure-actuated valve 24 is illustrated in FIG. 1 as a conventional, spring-loaded ball valve which is designed or adjusted to open at a predetermined small pressure rise in the high pressure carrier liquid conduit upstream of the valve 24. Thus, when the injection valve 16 is switched into the "sample load" position from any other position, all high pressure carrier liquid flow is directed immediately to the column through the pressure-actuated valve 24. The valve is set to open at a sufficiently low pressure rise in the upstream carrier liquid which is well below any liquid pressure variation which, if occurring in the column, would provide false information, mask or otherwise obscure analysis of the sample liquid. Correspondingly, when the injector valve is switched from the "sample load" to the "sample inject" position, pressure-actuated valve 24 immediately closes so that all of the high pressure carrier liquid is directed through the injection valve and sample loop to the column.

FIG. 8 illustrates the liquid flow path through the injection valve when the valve is in the "sample loop clean" position with rotor handle 36 located in the right-hand position, as shown in phantom lines, in FIG. 1. In this position, rotor ports 64 and 66 are aligned, respectively, with stator ports 89 and 88 to pass high pressure carrier liquid from the pumping means P through the sample loop L to waste D. Thus positioned, the sample loop can be completely cleaned of any previous sample before start up of a new sample analysis operation.

From the foregoing, it can be seen that the particular arrangement and construction of the sample injection valve and pressure-actuated valve of the present invention may be employed to introduce precisely measured amounts of sample liquid into a chromatography column for analysis without any substantial pressure or flow variations occurring in the column during sample analysis. The precise amount of sample liquid for introduction into the column is insured by preselecting a sample loop of desired volumetric size. The sample loops of various volumetric capacities may thus be connected to the rotor section of the injection valve to deliver various predetermined amounts of sample liquid for analysis. Also, the unique construction and arrangement of the sample injection valve and its gasket sealing means permits fast, reliable and leak-free sample introduction and operation of the chromatography system.

Although the foregoing relates only to a preferred embodiment of the present invention, it will be apparent that numerous alterations and modifications may be made therein without departing from the spirit and the scope of the present invention as set forth in the claims herein appended.

That which is claimed is:

1. In liquid chromatography apparatus for analyzing liquid samples including a liquid-separation column, pump means and conduit means for continuously delivering a carrier liquid to said column under a predetermined high pressure, and means positioned in said conduit means between said pump means and column for introducing a predetermined amount of liquid sample into the pressurized carrier liquid for passage into the column; the improvement wherein said sample introducing means comprises means for storing a determined amount of liquid sample; a sample injection valve connected to said sample storing means and to said conduit means and including means positionable for alternatively communicating (1) said storing means with a source of liquid sample and a discharge to waste, (2) said pump means with said column through said sample storing means, and (3) said pump means to a discharge to waste through said sample storing means; and pressure-actuated means positioned in said conduit means in parallel with said sample injection valve for passing carrier liquid directly from said pump means to said column only upon a predetermined small pressure increase above said predetermined high pressure occurring in said conduit means upstream of said pressure-actuated valve to thereby maintain substantially constant high pressure flow of carrier liquid to said column..

2. Apparatus as defined in claim 1 wherein said sample injection valve comprises a stator section and a rotor section, said stator section including a primary inlet connected to said pump means by said conduit means for receiving carrier liquid, a primary outlet connected to said column by said conduit means for delivering carrier liquid to said column, a secondary inlet for receiving an amount of sample liquid, and a secondary outlet for discharging liquid to waste; said rotor section including first and second passageways, said sample liquid storing means comprising an elongate conduit of fixed volume having opposite ends connected to respective end of said first and second passageways, and means for selectively positioning said rotor section to communicate said first and second passageways respectively with (1) said primary inlet and outlet, (2) said secondary outlet and inlet, and (3) said primary inlet and said secondary outlet.

3. Apparatus as defined in claim 2 wherein said stator section further includes an annular flat surface containing a plurality of ports positioned in arcuately spaced relation about the surface, a first of said ports communicating by a passageway with said primary inlet, a second of said ports communicating by a passageway with said secondary inlet, a third of said ports communicating by a passageway with said primary outlet, and a fourth of said ports communicating by a passageway with said secondary outlet, said rotor section further including a corresponding annular flat surface positioned in mating relation to said stator section flat surface and containing two ports arcuately spaced about said rotor surface communicating with said first and second rotor section passageways, and gasket means positioned between and in contiguous relation with said rotor surface and said stator surface to provide a liquid seal between ports of said rotor and stator surfaces which are not in selective alignment with each other.

4. Apparatus as defined in claim 3 wherein said stator flat surface has a relatively high coefficient of friction engaging said gasket means, and said rotor flat surface has a relatively low coefficient of friction engaging said gasket means to facilitate maintaining said gasket means in fixed position relative to said stator surface during rotation of said rotor section.

5. Apparatus as defined in claim 4 wherein said gasket means comprises a plastic impervious to said carrier liquid and having sufficient rigidity to maintain its shape under the pressure of said carrier liquid flow through said sample injection valve.

6. A rotary sample injection valve for delivering small measured amounts of sample liquid into a carrier liquid stream comprising a rotor section and a stator section having mating flat surfaces containing a plurality of ports, means for rotating said rotor section surface relative to said stator section surface to selectively communicate said ports, and gasket means positioned between said rotor and stator surfaces and having a first surface of relatively high coefficient of friction engaging said stator surface, and a second surface of relatively low coefficient of friction engaging said rotor surface whereby the fixed positioning of said gasket means relative to said stator surface is facilitated during rotation of said rotor section.

7. In a method for periodically injecting small predetermined amounts of sample liquid into a high pressure stream of carrier liquid for introduction into a liquid chromatography apparatus for analysis, the improvement comprising the steps of:
1. supplying carrier liquid under a predetermined high pressure in a primary flow path to said column;
2. periodically closing said primary flow path;
3. sensing a predetermined small upstream pressure increase in said pressurized carrier liquid when said primary flow path is closed;
4. immediately diverting all of said high pressure carrier liquid into a second flow path to said column in response to said small upstream pressure increase in said carrier liquid pressure in said primary flow path;
5. accumulating a predetermined amount of sample liquid in said primary flow path;
6. thereafter opening said primary flow path to introduce the accumulated sample liquid into said carrier liquid;
7. sensing a predetermined small upstream pressure decrease in said pressurized carrier liquid when said primary flow path is opened; and
8. immediately closing said second flow path in response to said small upstream pressure decrease to redirect all of said carrier liquid into the primary flow path and thereby maintain at all times a substantially constant high pressure flow of carrier liquid to said column.

8. A method as defined in claim 7 including the further step of periodically directing high pressure carrier liquid through said primary flow path to overflow to waste to clean said primary flow path prior to accumulation of a sample liquid therein.

9. In a liquid chromatography apparatus including a liquid-separation column, pump means and conduit means for continuously delivering a flow of carrier liquid to said column under a predetermined high pressure, and means positioned in said conduit means between said pump means and said column for introducing a predetermined amount of liquid sample into said pressurized carrier liquid for passage into said column; the improvement wherein said sample introducing means comprises:
   means for selectively blocking a primary flow path of said pressurized carrier liquid from said pump means to said column;
   normally closed pressure-actuated valve means for diverting the entire flow of said pressurized carrier liquid into a secondary flow path from said pump means to said column in response to a predetermined small pressure increase in said pressurized carrier liquid upstream of said blocking means when said primary flow path is blocked;
   means for storing a selected volume of liquid sample in said primary flow path when said primary flow path is blocked; and
   means for selectively re-opening said primary flow path whereby said volume of liquid sample is carried to said column by the entire flow of said pressurized carrier liquid;
   said pressure-actuated valve means closing to block said secondary flow path in response to a predetermined small pressure decrease in said pressurized carrier liquid upstream of said pressure-actuated valve when said primary flow path is re-opened, thereby maintaining a substantially constant high pressure flow of carrier liquid to said column.

* * * * *